Figure 1:
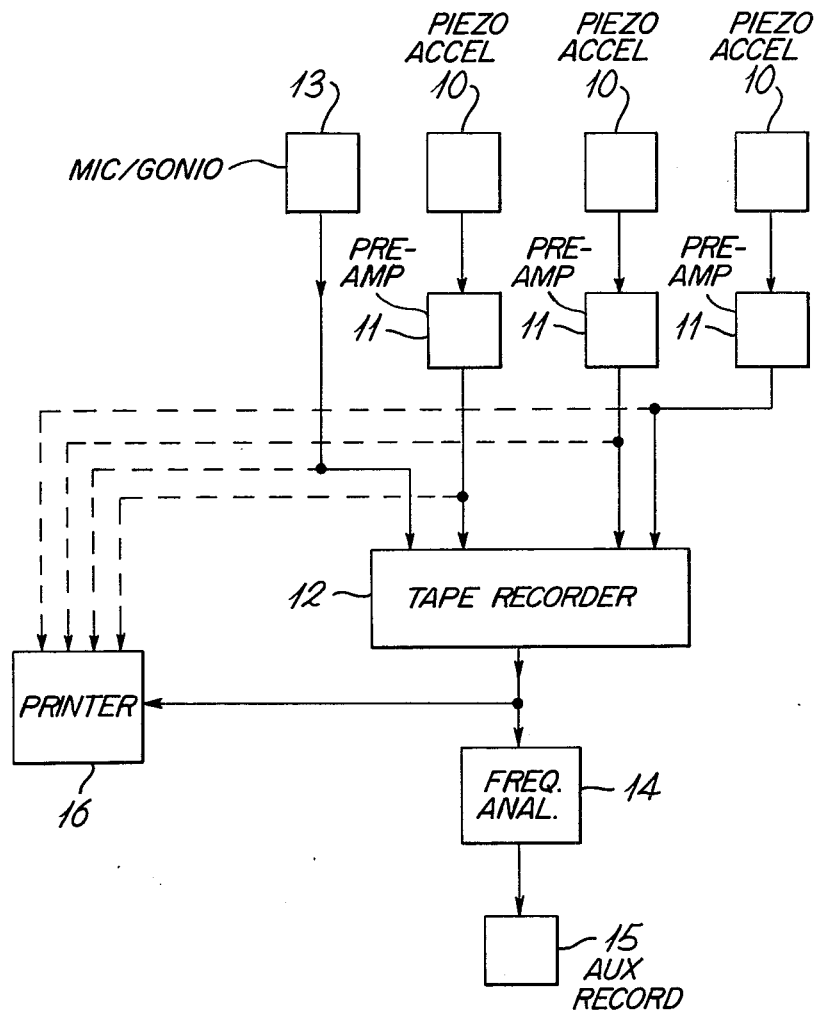

United States Patent [19]

Mollan

[11] 4,437,473
[45] Mar. 20, 1984

[54] ORTHOPEDIC DIAGNOSTIC PROCEDURES AND APPARATUS THEREFOR

[75] Inventor: Raymond A. B. Mollan, Holywood, Ireland

[73] Assignee: National Research Development Corporation, London, England

[21] Appl. No.: 362,516

[22] Filed: Mar. 26, 1982

[30] Foreign Application Priority Data

Apr. 3, 1981 [GB] United Kingdom ............. 8110528

[51] Int. Cl.³ .................................................. A61B 5/12
[52] U.S. Cl. ................................... 128/773; 128/774
[58] Field of Search ........................ 128/773, 715, 774

[56] References Cited

U.S. PATENT DOCUMENTS

| 3,181,528 | 5/1965 | Brackin | 128/773 |
| 3,985,121 | 10/1976 | Hellenbrand | 128/715 X |
| 4,008,711 | 2/1977 | Olinger et al. | 128/773 X |

FOREIGN PATENT DOCUMENTS

| 429748 | 6/1935 | United Kingdom | 128/773 |
| 1167655 | 6/1967 | United Kingdom |  |
| 1274687 | 6/1969 | United Kingdom |  |
| 1319054 | 6/1970 | United Kingdom |  |
| 1571643 | 8/1977 | United Kingdom |  |
| 304939 | 7/1971 | U.S.S.R. | 128/773 |

OTHER PUBLICATIONS

Bradley et al., Journal of Urology, vol. 118, 1977, pp. 73-75.
Anishkina et al., Biomed. Eng., vol. 12, No. 1, Sep. 1978.
Blinowska et al., Med. and Biol. Engr. and Comput., Mar. 1979, vol. 17, pp. 207-210.
Chu et al., Med. and Biol. Engr. & Comput. vol. 16, No. 4, Jul. 1978, pp. 437-442.
A Critical Appraisal of Auscultation of Human Joints, British Medical Journal—Congenital Hip Dislocation: An Increasing and Still Uncontrolled Disability?

*Primary Examiner*—Kyle L. Howell
*Assistant Examiner*—John C. Hamley
*Attorney, Agent, or Firm*—Cushman, Darby & Cushman

[57] ABSTRACT

Attempts have been made to facilitate orthopedic diagnostic procedures by microphonic detection of emissions from a moving joint, with analysis of such emissions to establish correlation with pathological conditions, but these attempts have failed. Success in such a procedure is now found to require detection of emissions extending into the subsonic frequency range. Preferably a piezoelectric accelerometer detector (10) is used in direct contact with the skin. A plurality of detectors can be used around a joint with comparative analysis to localize a condition. Analysis suitably involves a frequency analyzer (14) with the possible intermediary of a multi-track tape recorder (12), the analyzer output being displayed by a printer (15) preferably of ink-jet form. One useful correlating emission characteristic is peak frequency for early diagnosis for congenital dislocation of the hip in an infant.

6 Claims, 6 Drawing Figures

ORTHOPEDIC DIAGNOSTIC PROCEDURES AND APPARATUS THEREFOR

This invention concerns orthopaedic diagnostic procedures and apparatus therefor, and more particularly such procedures and apparatus for detecting and assessing pathological conditions in the joints.

One of the techniques employed in existing diagnostic procedures for pathological joints centres on the detection and interpretation of sound and crepitus emitted by the joint during movement. This technique has until now involved subjective clinical interpretation by the surgeon, who spends many years developing the skill which such interpretation requires.

Various attempts have been made to facilitate this technique by way of instrumental aids and there has been progress in the further past by the development of apparatus such as stethoscopes which aid the detection aspect of the technique. Even so, this development was initiated in respect of cardiovascular and respiratory diagnostic procedures and then translated, albeit with some modification, to orthopaedic usage.

More recent attempts at improvement directly related to orthopaedics have involved microphonic detection to generate electrical signals representing sound emissions from a joint, which signals can be recorded and analysed with a view to providing results which distinctively identify pathological conditions. However, these have failed to produce results which effectively and reliably aid interpretation in the desired manner.

The present invention has been developed following a further, detailed and extensive investigation of the microphone-based acoustic techniques. The result of this investigation was to establish that such techniques could not be improved to the point where they formed the basis for a routine clinical procedure.

Several factors led to this conclusion, these factors arising from the following findings:

(1) Ambient noise can give rise to sound signals at least as loud as those derived from the joint. This difficultly can be alleviated by resorting to the use of insulatory screening of the microphone and an anechoic room, but such precautions are unsuited to routine clinical practice.

(2) Sound emissions from a moving joint have predominant components at low frequencies and are part of a wider spectrum of emission extending into subsonic frequencies. Moreover such frequencies can be of high amplitude within the overall emission. This finding is most important because it explains the lack of success with microphonic detection in that the equipment will be inadequate in respect of frequency sensitivity and dynamic response.

(3) Relative movement and the associated friction at the detector/skin interface produces artefacts in the signals. These artefacts can be reduced by the use of a small detector, but in the case of a microphone this is likely to seriously constrain the quality of detection which, as indicated under (2) above, is already inadequate.

In the light of these factors it is now proposed that an improved orthopaedic diagnostic procedure and apparatus provide for detecting, preferably with a piezoelectric accelerometer, from a moving joint vibration emission extending into the subsonic frequency range, and analysing the detected emission to determine whether it has a characteristic of predetermined form indicative of a pathological condition.

A fuller understanding of the invention will be gained from the following description of the corresponding apparatus as so far developed and contemplated, this description being given by way of example and with reference to the accompanying drawings, in which:

FIG. 1 schematically illustrates one form of apparatus as so far developed according to the present invention; and FIGS. 2 to 6 graphically illustrate results attained with the apparatus of FIG. 1.

The apparatus of FIG. 1 comprises three piezoelectric accelerometers 10 having their outputs applied by way of individual preamplifiers 11 to respective tracks of a tape recorder 12. A further track of the recorder 12 can record the output of a microphone and/or goniometer 13 to provide a verbal commentary on the procedure and/or to denote the varying joint position. The tape recorder can apply its record outputs individually to a frequency analyser 14 having an auxiliary recorder 15. The tape recorder outputs can also, or the preamplifier outputs can directly, be applied in parallel to a multi-track printer 16.

It is to be understood that the form of apparatus of FIG. 1 has been primarily suited to development and is not necessarily to be regarded as commercial clinical equipment. However, some of the features suiting development may also suit practical clinical requirements. In particular the apparatus need not be used as a whole at any one time insofar as the components up to and including the tape recorder 12 can be transported to different locations in order to generate signal records for various subjects, and the remaining components used, with the tape recorder, or a duplicate thereof, thereafter for purposes of analysis at a central site. Also, the accelerometers, and correspondingly the associated preamplifiers and multi-track tape recorder, are employed in a multiple presence to allow simultaneous detection in mutually spaced positions adjacent to a joint and the consequent possibility of localisation of a condition within the joint. Such localisation can in fact be effected and this capability will be relevant to some clinical requirements.

Regarding the individual components of the apparatus, the accelerometers should be small and have suitable response characteristics in recognition of the findings (2) and (3) above. This presents no difficulty vis-a-vis available products. The same is true in respect of corresponding requirements in operational characteristic for the preamplifiers. However, one particular point arises over the choice between operating the accelerometers as capacitive or voltage sources. The former mode was preferred because the cables connecting the accelerometers and preamplifiers will have a capacitive effect which can be matched with the accelerometers and allow the convenience of long cables without affecting the lower frequency sensitivity of the accelerometers. This choice also requires the corresponding use of a charge type preamplifier.

In practice the accelerometers and preamplifiers so far used have been B & K Types 4344 and 2636, respectively.

The choice of tape recorder clearly involves a requirement for an appropriate multi-track facility and frequency response. A further requirement is the ability to replay at slow speeds to facilitate detailed analysis without loss of low frequency content. This is met by the use of a recorder which operates in the frequency modulation (FM) mode and in practice a B & K Type 7003 has been used.

The frequency analyser desirably provides a range of capabilities including display of the vibration signals in original time-amplitude mode and in frequency spectrum form as by Fourier transform, and averaging. The analyser used was a B & K Type 2031 which provides these capabilities, with exponential or linear averaging being available, plus, among other things, an adjustable trigger mode whereby corresponding portions of a cyclic input of continuous or intermittent form can be automatically selected for processing, and an interface facility (IEC 625-1) allowing digital transfer with compatable peripheral equipment.

The auxilliary recorder for the tape recorder was chosen as an X-Y printer, which in practice was of B & K Type 2308.

The printer is required to respond satisfactorily to rapidly changing signals containing high frequency components in excess of 100 Hz and a review of possibly suitable multi-track types show ink-jet forms to be preferable in affording this capability while producing an instantly visible permanent record. An additional benefit is that such printers are in common clinical usage in association with electrocardiographs (ECG). In practice, a Siemens-Elema Mingograf 34 has been employed.

A remaining point of a more general nature to be noted in connection with the apparatus of FIG. 1 concerns the manner of application of the accelerometer to a subject. Study was made of the differences between non-invasive application to the skin and invasive application directly to the bone. Two specific considerations are relevant from a practical point of view, as follows:

(a) Whether non-invasive application is sufficiently comparable with invasive application to provide results which are clinically useful, the initial presumption being that invasive application was likely to provide better results by avoiding the possibility of distortion, while at the same time being clearly less well suited to wide routine usage, and (b) Whether non-invasive application would require or benefit from the use of an adhesive or other coupling medium between the accelerometers and the skin.

Surprisingly, and beneficially, non-invasive application is found to provide results at least as good as invasive application, with signal components of interest being enhanced in the former case compared to the latter in many tests. Also, no material improvement was found to occur with use of a coupling medium. In the result non-invasive application directly to the skin with the accelerometers simply held in place by adhesive medical tape is satisfactory.

Development of the inventions has involved use of the apparatus described above and the last-mentioned mode of accelerometer application on numerous subjects in relation to various joints and conditions, and it has been established that results can be obtained which are consistent in a mutual sense, in comparison with traditional diagnostic procedures as deployed by experts, and in comparison with subsequent findings during surgery. These results involve the provision of data which conforms to a consistent pattern for a given bone joint species, and which contains consistent irregularities identifying abnormalities when present in an individual joint of a species. The general pattern for a joint species is found to be one of slow waves on which faster impulses and transients of relatively low amplitude are superimposed. Irregularities occur as prominent impulses and transients and these coincide with conventional detection of palpable crepitus. Moreover, the results can serve not only to detect and identify a pathological abnormality, but also to localise the same in the joint by comparison of the outputs from the accelerometers by spacing them around the joint.

Figure 2:
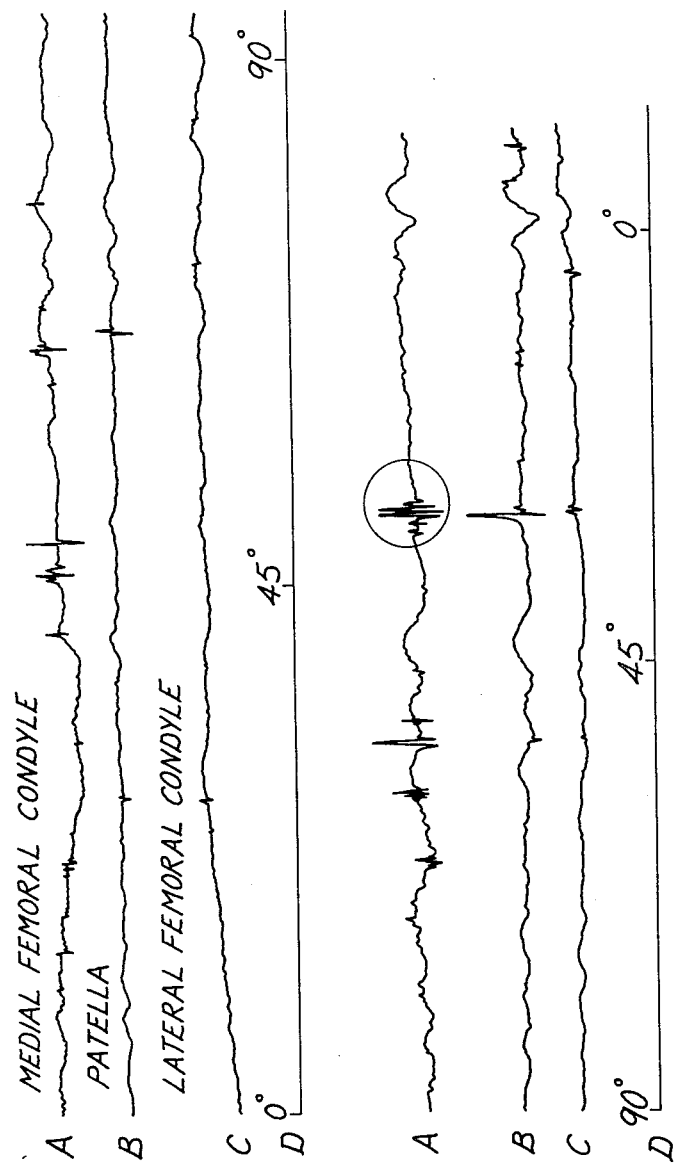

FIG. 2 illustrates such as just discussed in relation to the knee joint with a medial meniscal tear. This Figure is in four parts A to D of which the first three indicate the outputs from the accelerometers when located across the joint in the coronal plane adjacent the medial femoral condyle, the patella, and the tibial femoral condyle, respectively. The fourth part indicates movement of the joint from 0° to 90° flexion and back again. Irregularities of particular interest are the encircled transients which occur at about 30° flexion during the return movement, which transients indicate the meniscal tear and, by their relative magnitudes, localise the tear in the medial meniscus.

Figure 3:
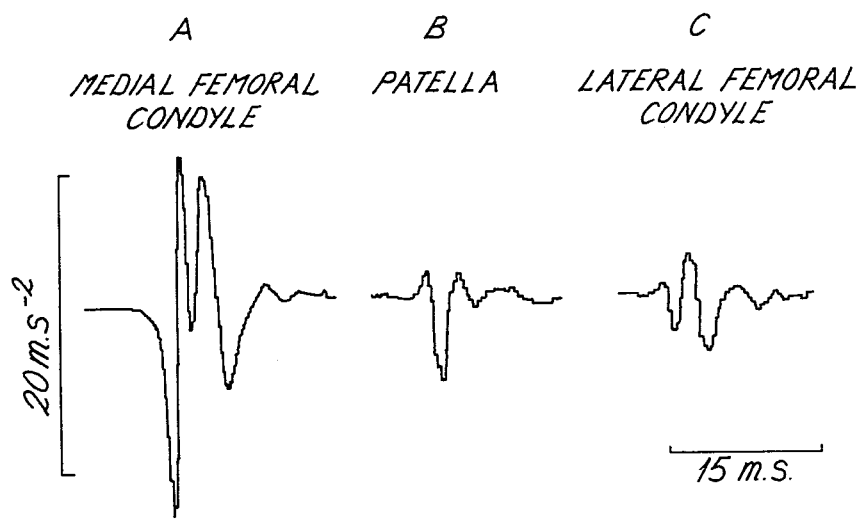

FIG. 3 illustrates similar results for a medial meniscal tear in another patient, only the transients, A, B and C being shown in this case.

Figure 4:
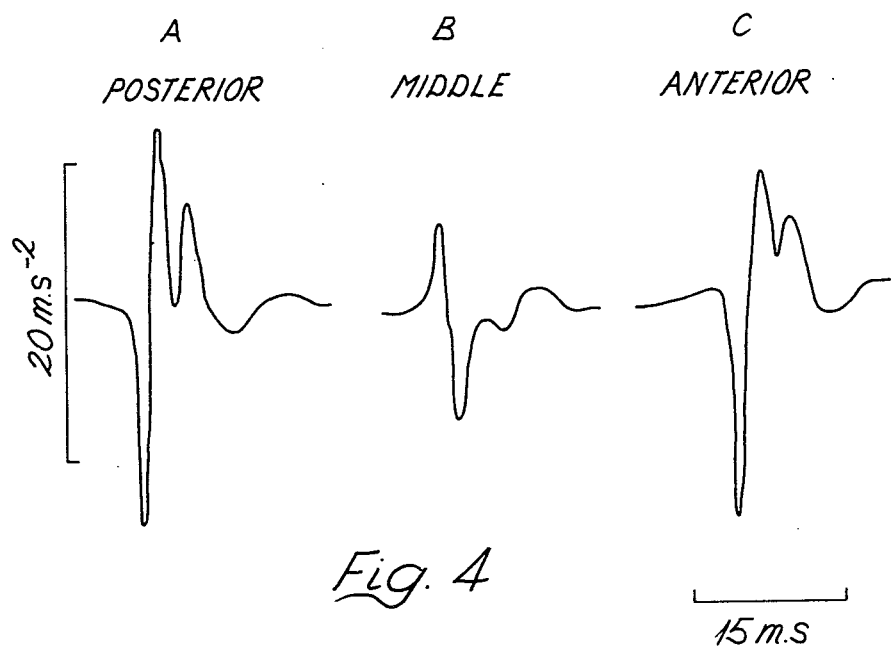

FIG. 4 concerns the same patient as FIG. 3 and shows transients A, B and C derived from the accelerometers when located to the posterior, middle and anterior of the medial tibial condyle in the transverse plane. These results localised the tear in the anterior portion of the meniscus by virtue of higher amplitude in transient C.

Detailed frequency analysis of the transients of interest shows a recurrent pattern of two superimposed frequencies which are though to be a driving frequency and an inherent or resonant frequency for the particular bone. Also the frequency increases from the region of 100 Hz as the originating vibration is transmitted across the joint.

This frequency increase suggests a reason for confusion that can arise in clinical practice. Often it is difficult to decide which side of the knee a meniscal impulse originates from even though other methods of examination may point to a particular side, and a patient may be subjected to an arthrotomy on both sides of the joint before the diagnosis is made, with the prolonged rehabilitation which is consequent on this procedure. It is now seen to be likely that the original impulse may not be audible because it is of low amplitude and at the lower end of the acoustic threshold. As the frequency rises with transmission across the joint, the threshold becomes exponentially lower and, even though the power may decrease, the frequency rapidly rises into the audible range.

Another area of diagnosis in which the invention has been developed is that of congenital dislocation of the hip (CDH). It is widely agreed that the earliest possible detection of this condition, in neonates, is desirable insofar as it is very much more readily corrected then than later. However, it is a fact that notwithstanding the existence of several diagnostic procedures and the application of these in varying degrees, many cases can be and are missed in the best of present circumstances, and the involvement of subjective interpretation as a key element can be assumed to be a cause of omissions. A new procedure involving a more objective determination and which is readily suited to screening application is accordingly desirable.

Figure 5:
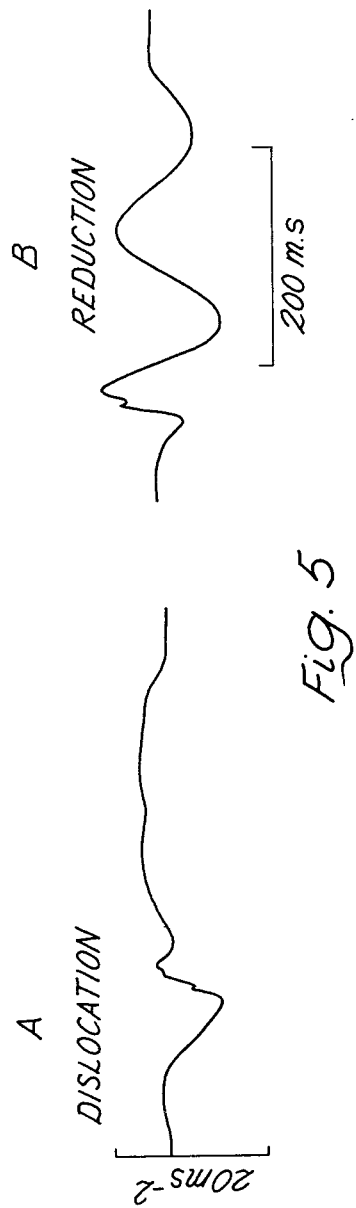

The present invention is considered to be applicable to this last purpose. In such application to date, multiple accelerometers have been sited in various locations around the infant pelvis, in contact with the sacrum and sacro-iliac areas, and also the anterior superior iliac spines and symphysis pubis. The former locations can be accomodated by housing the accelerometers in a board on which the infant is placed. Signal outputs followed a consistent pattern with dislocation of the joint being indicated by a low frequency displacement signal on which a high frequency component was superimposed at completion of the actual dislocation. This was followed by slow wave components of very low frequency and amplitude representing the dislocated femoral head in the pseudo-acetabular area. When the hip was reduced a small displacement signal was quickly followed by a high frequency component with reduction finally causing a resonating impulse to the pelvis represented by high amplitude low frequency waves which are slowly damped. FIG. 5 shows typical signal outputs during dislocation and reduction at A and B, respectively.

Frequency analysis shows the peak frequency at the sacrum to be in the region of 5 Hz for both events, while that on the anterior superior iliac spines is about double. The higher frequency components are represented at lower power levels on the side of the lesion under observation. It is probable that, as with knee joint lesions, a driving frequency and a natural frequency are present with the latter predominating further from the lesion.

Figure 6:
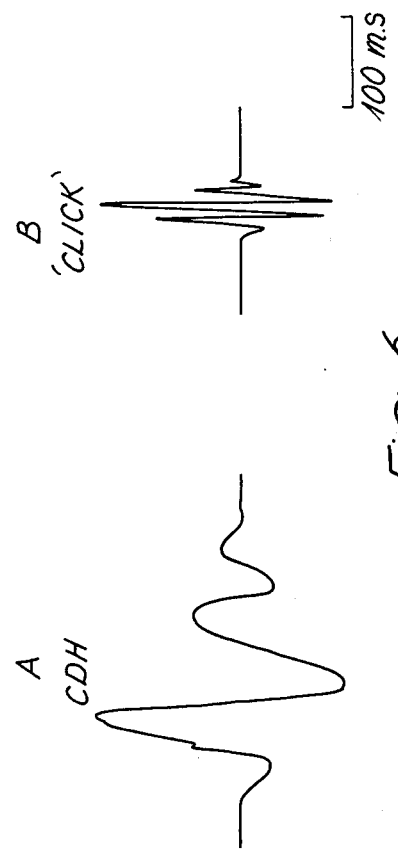

It is of interest to note that 'clicking' hips in neonates can be distinguished from CDH, the former giving rise to output signals of increasing and then decreasing sinusoidal form at a higher order of frequency, in the region of 400 Hz, compared to the latter. FIG. 6 shows comparable examples of CDH and click waveforms at A and B, respectively.

While the invention has been described with more particular reference to the illustrated apparatus and examples of results in relation to specific joint conditions, it has been made clear that the invention offers possibilities for variation and improvement. For example, the illustrated apparatus is constrained in usage by the fact that the frequency analyser must be used sequentially on different accelerometer signals, whereas a likely commercial development can involve simultaneous analysis by way of a microprocessor adapted to operate on the basis of comparison of results with predetermined patterns and parameters for a given joint species or condition.

I claim:

1. An orthopaedic diagnostic procedure comprising the steps of:
   detecting vibrations emitted from a moving joint in at least the subsonic frequency range, and
   analyzing the detected emissions to determine whether or not a predetermined pathological condition exists.

2. A procedure according to claim 1 where the step of detecting comprises detecting at a plurality of different positions around said joint, and comparing the emissions respectively detected from said positions to localise said condition in said joint.

3. A procedure according to claim 1 in which said joint is an infant hip joint and said condition is congenital dislocation of the hip.

4. A procedure according to claim 3 wherein said step of detecting comprises detecting emissions in at least two different positions in the areas of the sacrum, sacro-iliac, anterior superior iliac spines, and symphysis pubis.

5. A procedure according to claim 4 wherein said step of detecting comprises detecting a peak emission frequency in the region of 5 to 10 Hz.

6. A procedure according to claim 1 wherein said step of detecting comprises using a transducer is applied directly to the skin.

* * * * *